United States Patent [19]

Yu

[11] Patent Number: 5,872,000
[45] Date of Patent: Feb. 16, 1999

[54] NITRILASE GENE

[75] Inventor: Fujio Yu, Kanagawa, Japan

[73] Assignee: Nitto Chemical Industry Co., Ltd., Tokyo, Japan

[21] Appl. No.: 690,493

[22] Filed: Jul. 31, 1996

[30] Foreign Application Priority Data

Jul. 31, 1995 [JP] Japan .................................. 7-213061

[51] Int. Cl.⁶ .............................. C12N 1/21; C12P 19/34; C07H 21/04
[52] U.S. Cl. ................ 435/252.3; 435/91.2; 435/252.33; 536/23.2; 536/24.3
[58] Field of Search .................. 536/23.2, 24.3, 536/24.33; 435/252.3, 252.33

[56] References Cited

PUBLICATIONS

Kobayashi, M. et al. "Nitrilase from Rhodococcus rhodochrous J1" Journal of Biological Chemistry (Oct. 15, 1992), vol. 267, No. 29, pp. 10746–10751, Oct. 1992.

Primary Examiner—Rebecca E. Prouty
Assistant Examiner—Kawai Lau
Attorney, Agent, or Firm—Davidson, Davidson & Kappel, LLC

[57] ABSTRACT

The invention relates to a DNA coding for a polypeptide having nitrilase activity with an amino acid sequence as shown in SEQ ID NO:1. As compared with conventional processes, the hydrolysis of nitriles by a nitrilase gene cloned by genetic recombination is expected to drastically improve the catalytic ability of microorganisms because they can be engineered to contain multiple copies of the same gene.

14 Claims, 1 Drawing Sheet

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 344 amino acid residues
        ( B ) TYPE: amino acid
        ( D ) TOPOLOGY: linear ( i i ) MOLECULE TYPE: protein ( v i ) ORIGINAL SOURCE:
        ( A ) ORGANISM: Gordona terrae
        ( B ) STRAIN: MA-1
        ( C ) CELL TYPE: unicellular organism ( i x ) FEATURE:
        ( D ) OTHER INFORMATION: Xaa is Met or a deletion ( x i ) SEQUENCE DESCRIPTION: SEQ ID NO:1:

```
Xaa  Thr  Thr  Asp  Tyr  Ser  Gly  Thr  Phe  Lys  Ala  Ala  Val  Thr  Gln
 1                  5                        10                       15

Ala  Glu  Pro  Val  Trp  Phe  Asp  Leu  Ser  Ala  Thr  Val  Asp  Lys  Thr
                    20                       25                       30

Ile  Ala  Leu  Val  Glu  Glu  Ala  Ser  Arg  Ala  Gly  Ala  Asp  Leu  Ile
                    35                       40                       45

Ala  Phe  Pro  Glu  Thr  Trp  Ile  Pro  Gly  Tyr  Pro  Trp  Phe  Leu  Trp
                    50                       55                       60

Leu  Asp  Ser  Val  Ala  Trp  Gln  Ser  Gln  Tyr  Phe  Ile  Arg  Tyr  Pro
                    65                       70                       75

Gln  Asn  Ser  Leu  Asp  Leu  Asp  Gly  Ser  Glu  Phe  Ala  Ala  Ile  Arg
                    80                       85                       90

Glu  Ala  Ala  Arg  Lys  Asn  Asp  Ile  Ala  Ile  Thr  Met  Gly  Phe  Ser
                    95                       100                      105

Glu  Arg  Gly  His  Gly  Ser  Leu  Tyr  Met  Gly  Gln  Ala  Val  Ile  Glu
                    110                      115                      120

Arg  Asp  Gly  Val  Val  Val  Arg  Thr  Arg  Arg  Lys  Leu  Lys  Pro  Thr
```

|  |  |  | 125 |  |  |  |  | 130 |  |  |  |  | 135 |
|---|---|---|---|---|---|---|---|---|---|---|---|---|---|
| His | Val | Glu | Arg | Thr | Leu | Phe | Gly | Glu | Gly | Asp | Gly | Ser | Asp | Leu |
|  |  |  |  | 140 |  |  |  |  | 145 |  |  |  |  | 150 |
| Val | Val | Asp | Gln | Thr | Ser | Leu | Gly | Arg | Val | Gly | Ser | Leu | Cys | Cys |
|  |  |  |  | 155 |  |  |  |  | 160 |  |  |  |  | 165 |
| Trp | Glu | His | Leu | Gln | Pro | Leu | Thr | Lys | Tyr | Ala | Met | Tyr | Ser | Gln |
|  |  |  |  | 170 |  |  |  |  | 175 |  |  |  |  | 180 |
| His | Glu | Gln | Ile | His | Ile | Ala | Ala | Trp | Pro | Ser | Phe | Ser | Ile | Phe |
|  |  |  |  | 185 |  |  |  |  | 190 |  |  |  |  | 195 |
| Pro | Gly | Ala | Val | Tyr | Ala | Leu | Gly | Pro | Glu | Val | Asn | Thr | Ala | Ala |
|  |  |  |  | 200 |  |  |  |  | 205 |  |  |  |  | 210 |
| Ser | Gln | Gln | Tyr | Ala | Val | Glu | Gly | Gln | Thr | Tyr | Val | Leu | Ala | Pro |
|  |  |  |  | 215 |  |  |  |  | 220 |  |  |  |  | 225 |
| Cys | Ala | Val | Ile | Gly | Asp | Ala | Gly | Trp | Glu | Ala | Phe | Ala | Asp | Thr |
|  |  |  |  | 230 |  |  |  |  | 235 |  |  |  |  | 240 |
| Glu | Glu | Lys | Arg | Gln | Leu | Ile | His | Lys | Gly | Gly | Gly | Tyr | Ala | Arg |
|  |  |  |  | 245 |  |  |  |  | 250 |  |  |  |  | 255 |
| Ile | Tyr | Gly | Pro | Asp | Gly | Arg | Ser | Leu | Ala | Glu | Pro | Leu | Ala | Pro |
|  |  |  |  | 260 |  |  |  |  | 265 |  |  |  |  | 270 |
| Asn | Asp | Glu | Gly | Ile | Leu | Tyr | Ala | Asp | Ile | Asp | Leu | Ser | Ala | Ile |
|  |  |  |  | 275 |  |  |  |  | 280 |  |  |  |  | 285 |
| Leu | Ala | Ala | Lys | Asn | Pro | Ala | Asp | Pro | Val | Gly | His | Tyr | Ser | Arg |
|  |  |  |  | 290 |  |  |  |  | 295 |  |  |  |  | 300 |
| Pro | Asp | Val | Leu | Arg | Leu | Gly | Phe | Asn | Lys | Ala | Pro | Gln | Pro | Lys |
|  |  |  |  | 305 |  |  |  |  | 310 |  |  |  |  | 315 |
| Val | Asn | Ile | Leu | Gly | Thr | Glu | Pro | Ser | Arg | Thr | Thr | Ser | Thr | Gln |
|  |  |  |  | 320 |  |  |  |  | 325 |  |  |  |  | 330 |
| Cys | Arg | Pro | Thr | Thr | Ile | Arg | Arg | Ser | Trp | Arg | Phe | Pro | Glu |  |
|  |  |  |  | 335 |  |  |  |  | 340 |  |  |  |  |  |

( 2 ) INFORMATION FOR SEQ ID NO:2:

( i ) SEQUENCE CHARACTERISTICS:
        ( A ) LENGTH: 1035 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Gordona terrae
        ( B ) STRAIN: MA-1
        ( C ) CELL TYPE: unicellular organism ( x i ) SEQUENCE DESCRIPTION: SEQ ID NO:2:

ATG ACC ACC GAC TAT TCC GGC ACG TTC AAG GCA GCG GTG ACC CAG 45

GCC GAA CCG GTG TGG TTC GAC CTC TCG GCC ACC GTC GAC AAG ACC 90

ATT GCG CTC GTC GAA GAG GCG TCC CGG GCC GGC GCC GAT CTG ATC 135

GCG TTC CCG GAG ACC TGG ATA CCG GGG TAC CCG TGG TTC CTG TGG 180

CTT GAC TCG GTG GCC TGG CAG AGC CAG TAC TTC ATC CGG TAT CCG 225

CAG AAC TCG CTC GAT CTC GAC GGC AGC GAG TTC GCG GCG ATC AGG 270

GAA GCC GCA CGA AAG AAC GAC ATC GCG ATC ACC ATG GGA TTT AGT 315

GAG CGC GGT CAT GGT TCG CTG TAC ATG GGC CAG GCG GTC ATC GAG 360

CGT GAC GGG GTC GTC GTA CGC ACA CGC CGC AAA CTG AAG CCG ACC 405

| | | | | | | | | | | | | | | | |
|---|---|---|---|---|---|---|---|---|---|---|---|---|---|---|---|
|CAC|GTC|GAG|CGG|ACC|CTG|TTC|GGT|GAG|GGT|GAT|GGT|TCC|GAT|CTG|450|
|GTC|GTG|GAC|CAG|ACC|AGT|CTC|GGC|CGA|GTC|GGG|TCG|CTG|TGC|TGT|495|
|TGG|GAA|CAT|CTG|CAG|CCG|TTG|ACC|AAG|TAC|GCC|ATG|TAC|TCG|CAG|540|
|CAC|GAG|CAG|ATT|CAC|ATC|GCC|GCA|TGG|CCC|AGC|TTC|TCG|ATC|TTC|585|
|CCG|GGC|GCG|GTG|TAT|GCG|CTC|GGG|CCC|GAG|GTC|AAC|ACC|GCG|GCC|630|
|TCT|CAG|CAA|TAC|GCC|GTA|GAA|GGG|CAG|ACC|TAC|GTT|CTC|GCT|CCA|675|
|TGC|GCG|GTC|ATC|GGC|GAT|GCA|GGT|TGG|GAG|GCG|TTT|GCC|GAT|ACC|720|
|GAG|GAG|AAG|CGA|CAG|CTC|ATC|CAC|AAA|GGA|GGC|GGA|TAT|GCC|CGT|765|
|ATC|TAC|GGT|CCC|GAC|GGT|CGT|TCA|CTC|GCG|GAA|CCG|CTC|GCG|CCC|810|
|AAT|GAC|GAG|GGA|ATC|CTG|TAC|GCG|GAC|ATC|GAT|CTG|TCT|GCG|ATT|855|
|CTG|GCC|GCA|AAG|AAC|CCG|GCG|GAC|CCG|GTT|GGG|CAC|TAC|TCG|CGT|900|
|CCG|GAC|GTA|CTG|CGT|CTC|GGA|TTC|AAC|AAA|GCG|CCT|CAG|CCG|AAG|945|
|GTC|AAC|ATC|TTG|GGA|ACG|GAG|CCG|TCT|CGG|ACG|ACG|TCG|ACG|CAG|990|
|TGC|CGA|CCG|ACG|ACG|ATT|CGG|AGG|TCA|TGG|CGG|TTT|CCT|GAG|TGA|1035|

( 2 ) INFORMATION FOR SEQ ID NO:3:

( i ) SEQUENCE CHARACTERISTICS:
        ( A ) LENGTH: 1200 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Gordona terrae
        ( B ) STRAIN: MA-1
        ( C ) CELL TYPE: unicellular organism ( x i ) SEQUENCE DESCRIPTION: SEQ ID NO:3:

| | | | | | |
|---|---|---|---|---|---|
|GTTCAAAAAT|AGTCGATCGA|TCGTGCTGGC|AATGCTACGG|ACGTCGGCTG|50|
|TGACGCACCT|AACGTTGCTG|CCACCAACAA|AGAATGGAGT|CTCGATGACC|100|
|ACCGACTATT|CCGGCACGTT|CAAGGCAGCG|GTGACCCAGG|CCGAACCGGT|150|
|GTGGTTCGAC|CTCTCGGCCA|CCGTCGACAA|GACCATTGCG|CTCGTCGAAG|200|
|AGGCGTCCCG|GGCCGGCGCC|GATCTGATCG|CGTTCCCGGA|GACCTGGATA|250|
|CCGGGGTACC|CGTGGTTCCT|GTGGCTTGAC|TCGGTGGCCT|GGCAGAGCCA|300|
|GTACTTCATC|CGGTATCCGC|AGAACTCGCT|CGATCTCGAC|GGCAGCGAGT|350|
|TCGCGGCGAT|CAGGGAAGCC|GCACGAAAGA|ACGACATCGC|GATCACCATG|400|
|GGATTTAGTG|AGCGCGGTCA|TGGTTCGCTG|TACATGGGCC|AGGCGGTCAT|450|
|CGAGCGTGAC|GGGGTCGTCG|TACGCACACG|CCGCAAACTG|AAGCCGACCC|500|
|ACGTCGAGCG|GACCCTGTTC|GGTGAGGGTG|ATGGTTCCGA|TCTGGTCGTG|550|
|GACCAGACCA|GTCTCGGCCG|AGTCGGGTCG|CTGTGCTGTT|GGGAACATCT|600|
|GCAGCCGTTG|ACCAAGTACG|CCATGTACTC|GCAGCACGAG|CAGATTCACA|650|
|TCGCCGCATG|GCCCAGCTTC|TCGATCTTCC|CGGGCGCGGT|GTATGCGCTC|700|
|GGGCCCGAGG|TCAACACCGC|GGCCTCTCAG|CAATACGCCG|TAGAAGGGCA|750|
|GACCTACGTT|CTCGCTCCAT|GCGCGGTCAT|CGGCGATGCA|GGTTGGGAGG|800|
|CGTTTGCCGA|TACCGAGGAG|AAGCGACAGC|TCATCCACAA|AGGAGGCGGA|850|

-continued

| | | | | | |
|---|---|---|---|---|---|
| TATGCCCGTA | TCTACGGTCC | CGACGGTCGT | TCACTCGCGG | AACCGCTCGC | 900 |
| GCCCAATGAC | GAGGGAATCC | TGTACGCGGA | CATCGATCTG | TCTGCGATTC | 950 |
| TGGCCGCAAA | GAACCCGGCG | GACCCGGTTG | GGCACTACTC | GCGTCCGGAC | 1000 |
| GTACTGCGTC | TCGGATTCAA | CAAAGCGCCT | CAGCCGAAGG | TCAACATCTT | 1050 |
| GGGAACGGAG | CCGTCTCGGA | CGACGTCGAC | GCAGTGCCGA | CCGACGACGA | 1100 |
| TTCGGAGGTC | ATGGCGGTTT | CCTGAGTGAC | AAGGTGCTGG | CGACCGCCGC | 1150 |
| CGGAATGGCG | GAAAATCATC | AGTAATGGGC | GATTGCGCCA | CTCGTGCGCC | 1200 |

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

| | | |
|---|---|---|
| CGBCGBAARC | TSAARCCNAC | 20 |

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

| | | |
|---|---|---|
| GARTARTGRC | CSACVGGRTC | 20 |

NITRILASE GENE

FIELD OF THE INVENTION

The present invention relates to a novel polypeptide with nitrilase activity and a gene coding for the same.

BACKGROUND OF THE INVENTION

It is known that microorganisms or microorganism-derived enzymes can be used as catalysts in hydrolysis of nitrile compounds to produce carboxylic acids such as optically active α-hydroxy acids (see Japanese Laid-Open Patent Publication Nos. 99495/92, 99496/92, 218385/92(= U.S. Pat. No. 5,223,416, =EP-A- 0449648), 84198/90(=U.S. Pat. No. 5,283,193, =EP-B- 0348901), 99497/92(=U.S. Pat. No. 5,234,826, =EP-A- 0473328), 192189/93(=U.S. Pat. No. 5,326,702, =EP-A- 0486289), and 237789/94(=EP-A- 0610048)) and amino acids (see Japanese Laid-Open Patent Publication Nos. 317394/89, 117493/91, and 79894/92).

As compared with such conventional processes, the hydrolysis of nitriles by a nitrilase gene cloned by genetic recombination is expected to drastically improve the catalytic ability of microorganisms because they can be engineered to contain multiple copies of the same gene.

SUMMARY OF THE INVENTION

For the purpose of preparing a bacterial catalyst with higher catalytic activity, the present inventors cloned a nitrilase gene from *Gordona terrae* MA-1 to complete the present invention.

That is, the present invention relates to a novel polypeptide with nitrilase activity and DNA coding for the same. Further, this DNA may be an analog derived from degeneracy in the genetic code.

DETAILED DESCRIPTION OF THE INVENTION

Figure 1:
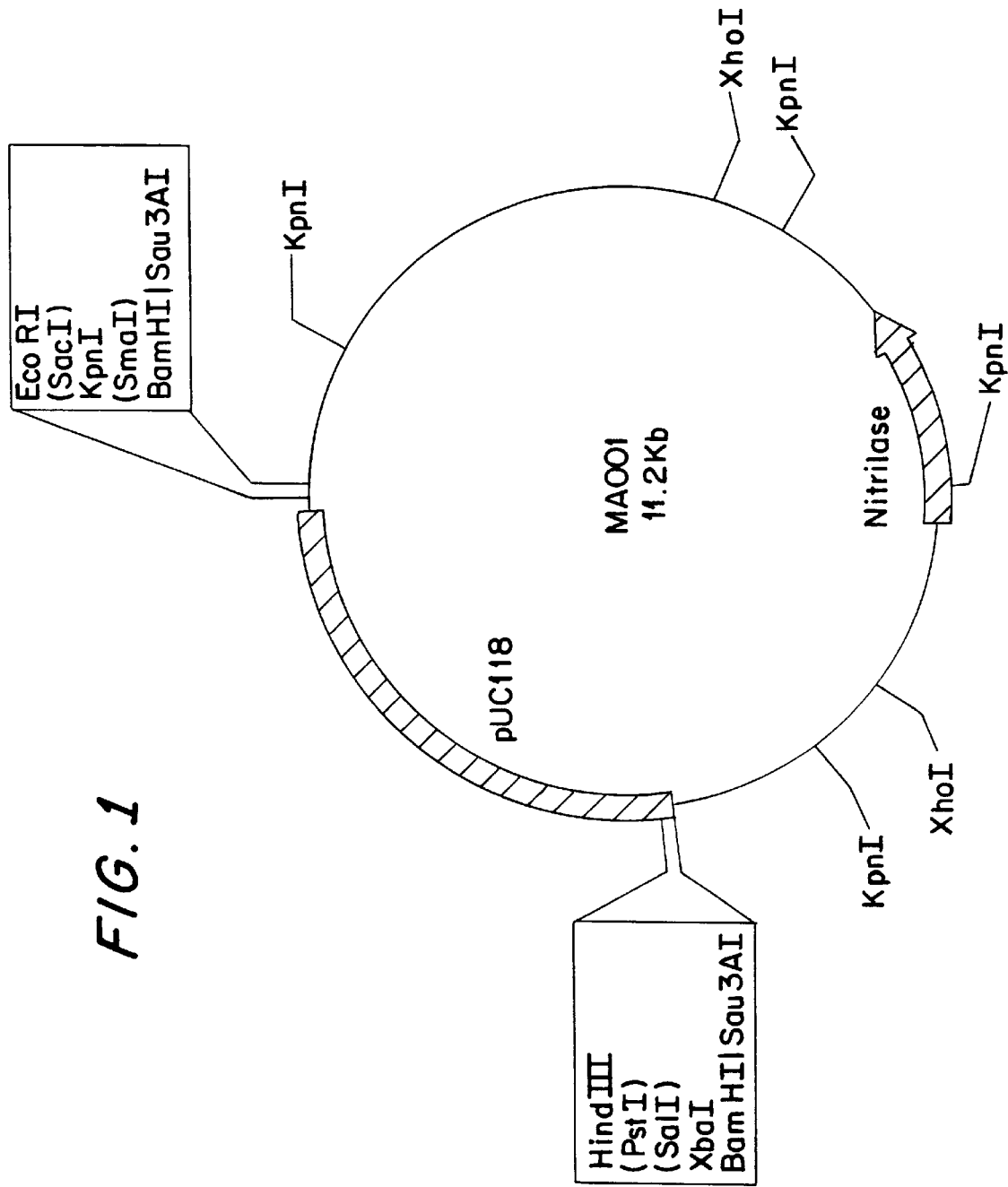
FIG. 1 shows a restriction enzyme map of pMA001 where the thick line indicates vector pUC118 and the thin line indicates the region of the MA-1-derived DNA. The arrow in the region of the MA-1 DNA indicates the location and direction of the nitrilase gene found in the present invention.

Hereinafter, the present invention is described in detail. The present invention is practiced in the following steps.

(1) Preparation of chromosomal DNA from *Gordona terrae* MA-1

Chromosomal DNA is isolated and prepared from MA-1.

(2) Preparation of a probe

Two kinds of synthetic DNA corresponding to partial sequences highly homologous among various nitrilases are prepared and used as primers in polymerase chain reaction (PCR) with the chromosomal DNA from MA-1 as a template whereby a part of a nitrilase gene is amplified. The DNA fragment thus amplified is used as a probe.

(3) Preparation of DNA Library

The chromosomal DNA is cleaved with restriction enzymes and the resulting fragments are inserted into plasmid vector pUC119 to give a library.

(4) Preparation of transformants and selection for recombinant DNA

The recombinant DNA library prepared in step (3) is used to transform Escherichia coli and the transformant is screened by colony hybridization using the DNA fragment obtained in step (2) as a probe to identify a transformant containing the target recombinant DNA.

(5) Preparation of a recombinant plasmid

A plasmid is prepared from the recombinant obtained in step (4).

(6) Preparation of a restriction enzyme map and identification of the region of the nitrilase gene A restriction enzyme map of the plasmid obtained in step (5) is prepared and the region (of the nitrilase gene) with which the probe is hybridized is identified.

(7) Nucleotide sequencing

The nucleotide sequence in the vicinity of the region identified in step (6) is determined.

The MA-1 strain has been deposited as *Gordona terrae* MA-1 (FERM BP-4535), and plasmid pMA001 containing the nitrilase gene has been deposited as transformant *E. coli* JM109/pMA001 (FERM BP-5547) containing the said gene, with the National Institute of Bioscience and Human-Technology, Agency of Industrial Science and Technology, Japan.

EFFECT OF THE INVENTION

As compared with conventional processes, the hydrolysis of nitriles by a nitrilase gene cloned by genetic recombination is expected to drastically improve the catalytic ability of microorganisms because they can be engineered to contain multiple copies of the same gene.

PREFERRED EMBODIMENTS OF THE INVENTION

The present invention is illustrated in detail by reference to the following examples, which however are not intended to limit the scope of the invention.

Example 1

(1) Preparation of chromosomal DNA from Gordona terrae MA-1

MA-1 was incubated at 30° C. for 72 hours under shaking in 100 ml MY medium (0.5% polypeptone, 0.3% Bacto yeast extract, 0.3% Bacto malt extract, 1% glucose). The cells were harvested and the pellet was suspended in 4 ml saline-EDTA solution (0.1M EDTA, 0.15M NaCl (pH 8.0)). 8 mg lysozyme was added to the suspension. The suspension was incubated at 37° C. for 1 to 2 hours and then frozen. 10 ml Tris-SDS solution (1% SDS, 0.1M NaCl, 0.1M Tris (pH 9.0)) was added to it under gentle shaking, then 0.1 mg proteinase K (a product of Merck) was added to it and the mixture was incubated at 37° C. for 1 hour. After an equal volume of TE-saturated phenol (TE: 10 mM Tris, 1 mM EDTA (pH 8.0)) was added, it was stirred and centrifuged. A 2-fold excess amount of ethanol was added to the supernatant. DNA thus precipitated was recovered with a glass rod, and the DNA was rinsed with 90%, 80%, and 70% ethanol in this order to wash off the phenol. Then, the DNA was dissolved in 3 ml TE. A solution of RNase A (previously treated at 100° C. for 15 minutes) was added to it to a final concentration of 10 μg/ml, and the mixture was incubated at 37° C. for 30 minutes. After proteinase K was added, the sample was incubated at 37° C. for 30 minutes. An equal amount of TE-saturated phenol was added to it, then the mixture was separated by centrifugation into upper and lower layers. The upper layer was subjected twice to the same procedure as above and extracted with an equal amount of chloroform containing 4% isoamyl alcohol in the same manner (these procedures are referred to hereinafter as phenol treatment). Then, a 2-fold excess amount of ethanol was added to it, and the DNA precipitated was recovered with a glass rod whereby the chromosomal DNA was obtained.

(2) Preparation of a probe

10 μl of the chromosomal DNA (20-fold dilution) obtained in step (1), 10 μl reaction buffer (10×), 3μl of 50 mM MgCl$_2$, 2 μl of 10 mM dNTP, 1 μl (100 pmol) each of an oligonucleotide as shown in SEQ. I.D. NO: 4 as primer #1 and an oligonucleotide as shown in SEQ. I.D. NO:5 as primer #2, and 1 μl Taq DNA polymerase (a product of GIBCO BRL) were mixed and the volume was brought up to 100 μl. The primers were constructed on the basis of amino acid sequences highly homologous among known nitrilases. This solution was incubated at 93° C. for 30 seconds (denaturation step), 55° C. for 30 seconds (annealing step) and 72° C. for 2 minutes (elongation step), and this cycle was repeated 30 times. After the reaction was finished, the amplification product was extracted 3 times with chloroform and precipitated with ethanol. The DNA thus recovered was separated by electrophoresis on 0.7% agarose gel whereby an about 500 bp (450 to 550 bp) DNA fragment considered to code for the MA-1 nitrilase gene was obtained. The DNA fragment thus obtained was labeled using DIG DNA Labeling Kit (Boehringer Mannheim) and used as a probe.

(3) Preparation of DNA library

50 μl of the chromosomal DNA from MA-1 was allowed to react at 37° C. for 10 to 20 minutes with a mixture of 10 μl reaction buffer (10 ×), 37 μl sterilized water and 0.5 μl restriction enzyme Sau 3AI, and DNA was recovered by ethanol precipitation. It was separated by agarose gel electrophoresis and DNA fragments of 6 kb or more were cut off from the gel and recovered with DNA PREP (K.K. Dia Yatoron). These DNA fragments were inserted into the Bam HI site of an E. coli vector pUC118 fragment using a ligation kit (Takara Shuzo Co., Ltd.) whereby a recombinant DNA library was obtained.

The pUC118 fragment used in the ligation was prepared in the following manner.

10 μl of pUC118 was allowed to react at 37° C. for 2 hours with a mixture of 10 μl reaction buffer (10 ×), 77 μl sterilized water and 2 μl restriction enzyme Bam HI, and the fragment was subjected to phenol treatment, then precipitated with ethanol, dried and dissolved in 50 μl sterilized water. It was further allowed to react at 65° C. with a mixture of 1 μl alkaline phosphatase (Takara Shuzo Co., Ltd.), 10 μl reaction buffer (10 ×) and 39 μl sterilized water. The fragment was subjected to phenol treatment, then precipitated with ethanol, dried, and dissolved in sterilized water.

(4) Preparation of transformants and selection for recombinant DNA

E. coli JM109 was inoculated into 1 ml LB medium (1 % Bacto trypton, 0.5% Bacto yeast extract, 0.5% NaCl) and incubated at 37° C. for 5 hours. 100 μl of the culture was added to 50 ml SOB medium (2% Bacto trypton, 0.5% Bacto yeast extract, 10 mM NaCl, 2.5 mM KCl, 1 mM MgSO$_4$, 1 mM MgCl$_2$) and cultured at 18° C. for 20 hours. The cells were harvested by centrifugation, and 13 ml of cold TF solution (20 mM PIPES-KOH (pH 6.0), 200 mM KCl, 10 mM CaCl$_2$, 40 mM MnCl$_2$) was added to the pellet. The pellet was allowed to stand at 0° C. for 10 minutes and centrifuged again. The supernatant was removed and the precipitate of E. coli was suspended in 3.2 ml of cold TF solution. 0.22 ml dimethyl sulfoxide was added to the suspension and it was allowed to stand at 0° C. for 10 minutes. 10 μl of the recombinant plasmids (DNA library) obtained in step (3) was added to 200 μl of the competent cells thus prepared. The mixture was allowed to stand at 0° C. for 30 minutes, then heat-shocked at 42° C. for 30 seconds and cooled at 0° C. for 2 minutes, followed by addition of 0.8 ml SOC medium (2% Bacto tryptone, 0.5% Bacto yeast extract, 20 mM glucose, 10 mM NaCl, 2.5 ml KCl, 1 mM MgSO$_4$, 1 mM MgCl$_2$). The mixture was incubated at 37° C. for 60 minutes with shaking. The culture, 200 μl per plate, was plated on an LB agar plate containing 100 μg/ml ampicillin. The plate was incubated at 37° C. To select a transformant having a nitrilase gene, the colonies grown on the plate were subjected to colony hybridization as follows: The colonies grown on the plate were transferred to a nylon membrane (Biodain A produced by Nippon Paul K.K.) and the microorganisms were lysed. The DNA was fixed on the membrane and then subjected to hybridization with the probe (about 500 kb fragment) obtained in step (2). A transformant having the target recombinant DNA was selected using DIG Luminescent Detection Kit (Boehringer Mannheim).

(5) Preparation of a recombinant plasmid

The transformant selected in step (4) was cultured at 37° C. overnight in 100 ml LB medium, then collected and washed with sterilized water. 5 ml of solution I (2 mM glucose, 10 mM EDTA, 25 mM Tris-HCl (pH 8.0)) and 25 mg lysozyme were added to the cells. The mixture was allowed to stand at 0° C. for 30 minutes. 10 ml of solution II (1N NaOH, 5% SDS) was added to the mixture. The mixture was allowed to stand at 0° C. for 5 minutes. 7.5 ml of solution III (3M sodium acetate (pH 4.8)) was added to the mixture. The mixture was allowed to stand at 0° C. for 30 minutes. The mixture was then centrifuged, then 50 ml ethanol was added to the supernatant, and the supernatant was removed by centrifugation. 5 ml of solution IV (10 mM sodium acetate, 50 mM Tris-HCl (pH 8.0)) and 2.5 μl solution (10 mg/ml) of RNase A were added to it, and it was allowed to stand at room temperature for 20 minutes. 12 ml ethanol was added to it, and the plasmid was recovered by centrifugation and rinsed with 70% ethanol, dried, and dissolved in 0.4 ml sterilized water. The solution was subjected to phenol treatment and the plasmid was recovered by precipitation with ethanol, dried, and dissolved in 0.4 ml sterilized water. The resulting recombinant plasmid was designated pMA001.

(6) Preparation of a restriction enzyme map and identification of the region of the nitrilase gene The plasmid pMA001 obtained in step (5) was cleaved with several restriction enzymes to prepare its restriction enzyme map (FIG. 1). Separately, pMA001 was cleaved with restriction enzymes such as Kpn I, Xho I, Pst I, Sal I etc. and the fragments were subjected to agarose gel electrophoresis. The fragment hybridized with the probe was identified by Southern hybridization.

(7) Nucleotide sequencing

The nucleotide sequence in the vicinity of the region identified in step (6) was determined by Fluorescence Sequencer ALF II (Pharmacia). The result indicated the presence of a nucleotide sequence as shown in SEQ. I.D. NO: 3, and there was found an open reading frame coding for an amino acid sequence as shown in SEQ. I.D. NO: 1. Comparison with amino acid data base NBRF (National Biomedical Research Foundation) revealed that this gene has 30 to 50% homologies with known nitrilases at the amino acid sequence level, and that this nitrilase also has highly homologous regions in common with known nitrilases, suggesting that this nitrilase is a novel nitrilase. The nucleotide sequence of the open reading frame is shown in SEQ. I.D. NO: 2.

Example 2

MA-1 was aerobically cultured at 30° C. for 72 hours in a medium (20 g/l glycerol, 3 g/l yeast extract, 6.8 g/l potassium monophosphate, 7.1 g/l sodium diphosphate, 2.8 g/l sodium sulfate, 0.4 g/l magnesium chloride, 0.04 g/l calcium chloride, 0.03 g/l manganese sulfate, 0.006 g/l iron chloride, 0.003 g/l zinc sulfate, 0.5 g/l benzyl cyanide). The cells were harvested by centrifugation, and the pellet was washed with 50 mM phosphate buffer (pH 8.2) and suspended in the same buffer. The cells were disrupted by sonication and centrifuged to give a supernatant (cell extract). A part of the supernatant was subjected to SDS polyacrylamide gel electrophoresis (SDS-PAGE) and the protein was transferred to PVDF membrane (Immobilon $P^S_Q$ (a product of Millipore)). The membrane was stained with Coomassie Blue, and a band with a molecular weight of about 40 kDa appearing only where an inducer was added to the medium was cut off, and its N-terminal amino acid sequence was analyzed by PSQ-1 Amino Acid Sequence Analyzer manufactured by Shimadzu Corporation. The sequence Thr-Thr-Asp-Tyr-Ser thus obtained agreed with the N-terminal amino acid (excluding N-terminal residue Met) deduced from the nucleotide sequence (SEQ. I.D. NO: 2). In addition, analysis of the amino acid sequence suggested that the N-terminal residue Met is not cleaved off and remains.

Various publications are referenced herein, the disclosures of which are incorporated by reference herein in their entireties.

What is claimed is:

1. An isolated DNA molecule comprising a coding sequence which encodes a polypeptide having an amino acid sequence as set forth in SEQ. I.D. No: 1, said polypeptide having nitrilase activity.

2. The DNA molecule according to claim 1 wherein the isolated DNA molecule comprises a nucleotide sequence as shown in SEQ. I.D. NO: 2.

3. An isolated DNA molecule which hybridizes to the nucleotide sequence as set forth in SEQ. I.D. NO: 2 under conditions favoring hybridization wherein the DNA molecule encodes the polypeptide of claim 1.

4. A recombinant host cell comprising at least one copy of the DNA molecule according to claim 1 that is able to express said polypeptide having nitrilase activity.

5. The recombinant host cell of claim 4 wherein the isolated DNA molecule comprises a nucleotide sequence as shown in SEQ. I.D. NO: 2.

6. A recombinant host cell comprising at least one copy of the DNA molecule according to claim 3 and that is able to express said polypeptide having nitrilase activity.

7. The recombinant host cell of claim 4 wherein the host cell is a microorganism.

8. The recombinant host cell of claim 6 wherein the host cell is a microorganism.

9. The recombinant host cell of claim 4 wherein a plasmid comprises the isolated DNA molecule.

10. The recombinant host cell of claim 9 wherein the plasmid is pMA001.

11. The recombinant host cell of claim 7 wherein the microorganism is *Escherichia coli*.

12. A DNA molecule comprising 450 to 550 base pairs, said DNA molecule obtained by amplifying a genomic DNA of *Gordona terrae* with synthetic DNAs having sequences shown in SEQ. I.D. NOS:4 and 5, under the following amplification conditions: a denaturing temperature of 93° C. for 30 seconds; an annealing temperature of 55° C. for 30 seconds; and an elongation temperature of 72° C. for 2 minutes.

13. The DNA molecule of claim 12 wherein the amplification cycle is repeated 30 times.

14. A recombinant host cell comprising a plasmid comprising an isolated DNA molecule comprising a coding sequence which encodes a polypeptide having an amino acid sequence as set forth in SEQ. I.D. NO: 1, said polypeptide having nitrilase activity and said plasmid being pMA 001.

* * * * *